United States Patent [19]

Brenner

[11] Patent Number: 4,579,452
[45] Date of Patent: Apr. 1, 1986

[54] PLASMA HEAT SHIELD FOR SPECTROPHOTOMETER

[75] Inventor: George D. Brenner, Blackheath, Australia

[73] Assignee: The Coca-Cola Company, Atlanta, Ga.

[21] Appl. No.: 570,717

[22] Filed: Jan. 13, 1984

[51] Int. Cl.⁴ .................................... G01N 21/73
[52] U.S. Cl. ............................ 356/316; 313/231.41
[58] Field of Search ...... 219/121 P, 121 PL, 121 PG; 313/231.41, 362.1; 356/315, 316

[56] References Cited

U.S. PATENT DOCUMENTS

| | | | |
|---|---|---|---|
| 3,931,542 | 1/1976 | Sheer et al. | 219/121 P |
| 4,009,413 | 2/1977 | Elliott et al. | 356/316 |
| 4,080,550 | 3/1978 | Sheer et al. | 219/121 P |
| 4,147,957 | 4/1979 | Hildebrand | 356/316 |

OTHER PUBLICATIONS

Owen, *Developments in Applied Spectroscopy*, vol. 1, 1962, p. 143

Primary Examiner—F. L. Evans
Assistant Examiner—Joel L. Harringa
Attorney, Agent, or Firm—Thomas R. Boston; Eduardo M. Carreras

[57] ABSTRACT

A heat shield for a sample introduction tube for a plasma jet device is disclosed, comprising a hollow cylindrical member disposed around the sample introduction tube, the hollow cylindrical member is provided with a reflective exterior and heat dissipating fins.

9 Claims, 4 Drawing Figures

PLASMA HEAT SHIELD FOR
SPECTROPHOTOMETER

BACKGROUND OF THE INVENTION

The invention relates to the field of plasma jet spectrophotometry, and more particularly to an improved sample introduction tube including a heat shield and radiant heat insulation.

Various plasma jet devices have been developed to generate a plasma jet for spectrometric analysis, or for studies of high-temperature chemical and physical phenomena of various materials. Generally, a plasma jet spectrophotometer includes a plasma jet device having a reaction or excitation zone which is stabilized in position. The reaction or excitation zone is obtained from the employment of a pair of electrodes of one polarity in combination with a third electrode of a different and opposite polarity than the first pair of electrodes. Generally, the electrodes in the first pair of electrodes are spaced apart in a position such that their axes, if extended, would intersect at an angle of anywhere from 60 to 90 degrees, while the third electrode is spaced apart from the angle of intersection of the first pair of electrodes and is offset from the plane formed by the intersecting axes, and typically and preferably offset substantially at right angles from the plane so as to form in operation a plasma jet of a column of ionized gas between electrodes, with the plasma jet being characterized by an inverted Y-form. The excitation or reaction zone in the Y-shaped plasma jet is formed at the lower region of the intersection of the extended axis of the first pair of electrodes. Such a plasma jet device is described in U.S. Pat. No. 4,147,957 issued on Apr. 3, 1979. As described in the referenced patent, directly below the intersecting angles of the first two electrodes, there is usually disposed a nebulizer or aerosol sample introduction tube having an outlet through which a sample of material can be placed in aerosol form in a gas stream. The device includes two constant current dc power supplies which provide power to the three electrodes of the device. In operation laminar flow of an ionized gas is maintained around the three electrodes. A sample material is then introduced as a laminar flow of an aerosol in an argon carrier through the nebulizer or aerosol sample introduction tube, and the outlet directly into the excitation zone formed by the plasma jet of the device. In a plasma jet the heated gas may reach a temperature in the region of 50,000 degrees Fahrenheit. Generally, the plasma jet at that temperature transfers heat to the sample introduction tube by three processes:

(1) Conduction, i.e. the transfer of heat from one part of the body to another part or to another body by short-range interaction of molecules and/or electrons;

(2) Convection, i.e. the transfer of heat by the combined mechanisms of fluid mixing and conduction; and (3) Radiation, i.e. the transmission of energy in the form of electromagnetic waves.

Radiation incident on the sample introduction tube is generally absorbed resulting in high temperatures, and as can be appreciated from the very high temperature of the plasma jet, a substantial amount of the heat transfer to the sample introduction tube is in the form of radiant-heat transfer.

One of the disadvantages of the conventional plasma jet assembly is that the sample introduction tube is disposed in close proximity to the excitation zone. Under normal conditions, when only inorganic solids are dissolved in a liquid phase, the solids are not greatly affected by the radiant, convective and conductive heat transfer to the sample introduction tube. However, if the dissolved solids are organic in character, for example sugar, there is a tendency for solids to decompose (e.g. the sugar will caramelize) and form globules just inside the tip of the sample introduction tube. When this happens, the uniform laminar flow necessary for the proper operation of the system will be disturbed thereby deviating the path of the sample stream and in turn, altering the results.

In U.S. Pat. No. 4,080,550 a plasma generator having a cooled annular cathode is disclosed. In the device a plurality of cooling passages surrounding the outlet orifice disposed within the annular cathode are disclosed. The passages are designed to maintain the temperature of the outlet orifice below the agglomeration temperature of the solids and the solids containing fluid medium being injected through the linear feed channels of the device. The cooling passages provide extensive cooling of the orifice outlets. Although this type of cooling arrangement is practical in conjunction with a conical cathode, such a cooling unit cannot be efficiently used with the plasma jet device and described in U.S. Pat. No. 4,147,957. There, the anodes are not conical but rather rectilinear and disposed in close proximity to sample introduction tube.

Numerous other plasma generation devices have been disclosed in the art, for example, U.S. Pat. No. 3,614,376 (Manabe, et al.); U.S. Pat. No. 3,818,174 (Camacho); and U.S. Pat. No. 3,858,072 (Dembovsky). These devices include some description of electrical insulation of the electrodes, and ways of stabilizing the flow of the gas stream, but do not describe an adequate means of insulating the sample introduction tube from the radiant and other heat transfer from the reaction zone.

It is accordingly an object of the present invention to provide a means for insulating the sample introduction tube from radiative, convective and conductive heat transfer from the plasma reaction zone.

It is another object of the present invention to provide a means for preventing agglomeration of organic matter in a sample introduction tube of a plasma jet in a spectrophotometer.

It is another object of the present invention to accomplish the aforementioned object without substantial or permanent modification to the equipment and without additional expensive equipment.

SUMMARY OF THE INVENTION

The aforementioned objects and other objects of the invention are accomplished by a heat shield member for the sample introduction tube of the spectrophotometer. The heat shield member comprises a cylindrical member having a tapering end portion with a circular opening adapted to be disposed over the sample introduction tube. The cylindrical member is provided with a plurality of radial openings around its periphery and is provided with a reflective coating adapted to reflect a substantial portion of the radiant energy generated by the plasma reaction zone.

BRIEF DESCRIPTION OF THE DRAWINGS

The objects and attendant advantages of the present invention will become more readily apparent by reference to the accompanying drawings in which.

DESCRIPTION OF THE EMBODIMENTS

Figure 1:
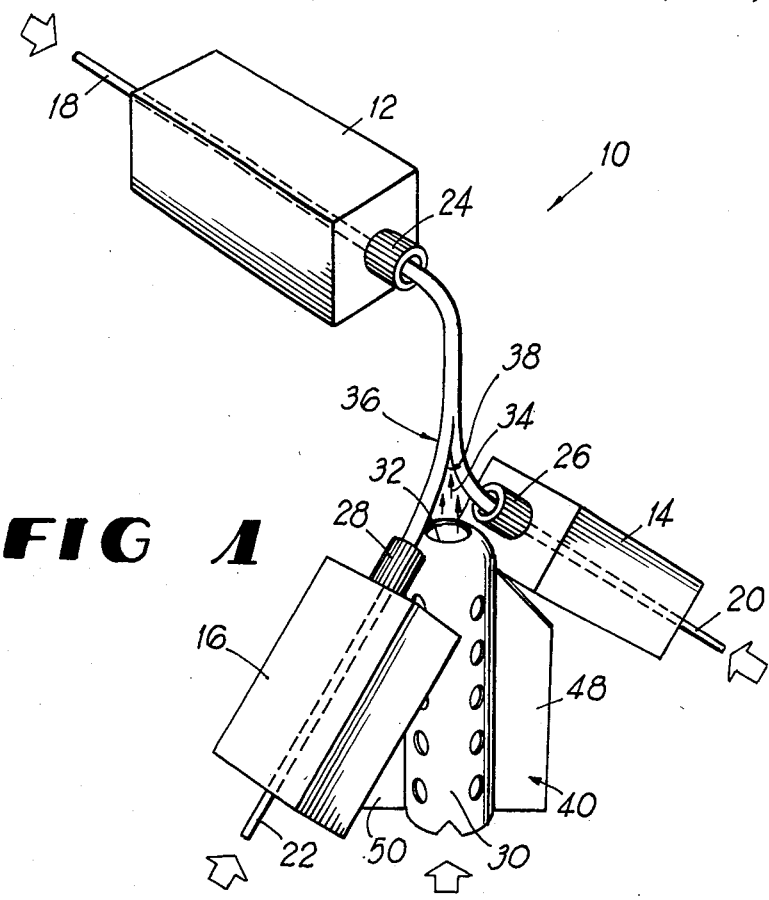
FIG. 1 is a schematic representative view of a plasma jet device with the heat sink of the present invention.

Illustrated in FIG. 1 is a plasma jet device 10 to be incorporated into a spectrophotometer. The jet device comprises a plurality of support members 12, 14 and 16 which incorporate the electrodes of the plasma jet device 10. Support means 14 and 16 surround a pair of anodes electrodes 20 and 22 which are typically made of graphite or tungsten, and which are disposed longitudinally along intersecting axes. Disposed within the supporting member 12 is a cathode 18. The cathode 18 and the anodes 20 and 22 are surrounded at their distal end by a ceramic coaxial sleeve 24, 26 and 28. Disposed directly below the intersecting axis of the electrodes 20 and 22 is a nebulizer or sample introduction tube 30, having an outlet opening 32. An ionizable gas such as argon is introduced into one end of each ceramic sleeve element and flows about the electrodes in the respective sleeve to form in operation the plasma jet 36. In operation, sample material is placed in aerosol form in a gas stream and introduced through the outlet 32 directly into an excitation region 38 of the plasma jet 36 formed by the electrodes. The plasma jet 36 as illustrated in FIG. 1, is in the form of an inverted Y. The plasma jet 36 is created by the electrical current flowing through the respective electrodes.

In operation, laminar flow of ionized gas is maintain around the electrodes 18, 20 and 22 while the sample material 34 is introduced as a laminar flow of an aerosol in an argon carrier through the sample introduction tube 30 and the outlet 32 directly into the excitation zone 38 formed by the plasma jet 36. The plasma jet formed will follow the flow of the ionized gas from the sleeve element 26 and 28 of the anodes 20 and 22, due to the magnetic attraction produced by current flowing in the same direction from each anode electrode. The excitation zone 38, as illustrated in FIG. 1, is between and just below the point where the two plasma columns of ionized argon from the anode electrodes 20 and 22 combine at that point of intersection.

A substantial portion of the energy provided to the plasma jet is released in the form of electromagnetic energy which can be absorbed by the various components of the plasma jet device 10. The intense radiance of the electromagnetic energy from the plasma jet can create high temperatures in the sample introduction tube 30. Accordingly a removable plasma heat shield 40 is provided as illustrated in FIG. 1, to surround the sample introduction tube insulating the sample from the heat transfer due to radiation, convection and conduction.

Figure 2:
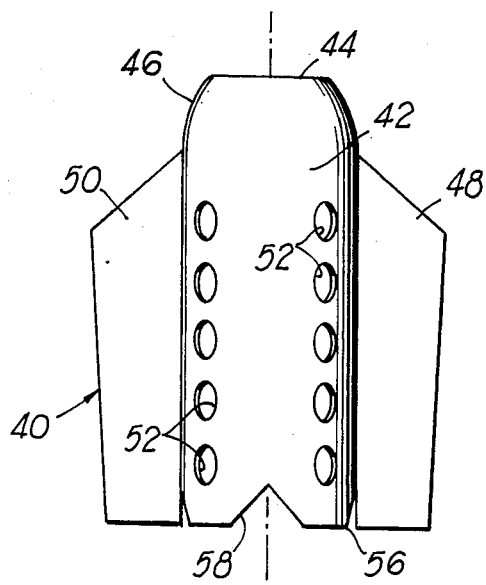
FIG. 2 is a front view of the plasma heat sink of the present invention.
Figure 3:
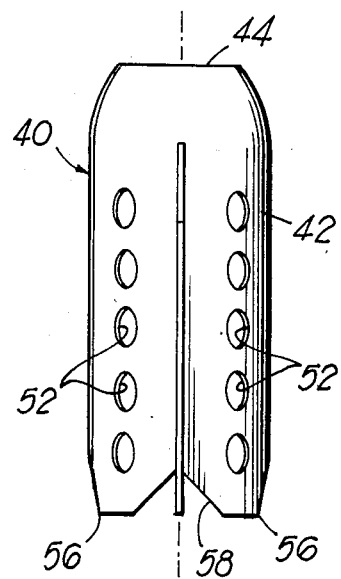
FIG. 3 is a side-view of the plasma heat sink of the present invention.
Figure 4:
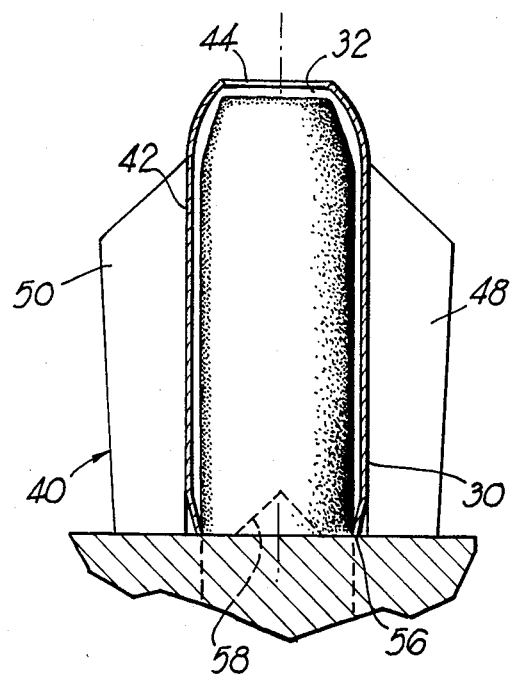
FIG. 4 is a cross-sectional view of the plasma heat sink of the present invention.

The heat shield 40 is illustrated in greater detail in FIGS. 2, 3 and 4. The heat shield 40 comprises an elongated cylindrical member 42 having a circular opening 44 at the distal end. The circular opening 44 is generally of smaller diameter than the inside diameter of the cylindrical portion 42 and a gradual transition zone between the two diameters is provided by curved portion 46. Attached along the major portion of the cylindrical member 42 are at least two fins 48 and 50. The fins 48 and 50 comprise a plate having one side attached to the cylindrical portion 42. The distal end of the fins may be provided with a sweep angle so as to minimize any aerodynamic interference with the laminar flow system of the plasma jet 10. The cylindrical portion 42 is provided with a plurality of holes or openings 52 which would serve to dissipate some of the hot gases which may be entrapped between the sample introduction tube 30 and the cylindrical portion 32. The fins 48 also serve to dissipate some of the heat by convective heat transfer with the surrounding environment as well as providing a heat sink for the large amount of electromatic energy absorbed by the heat shield 40. The exterior portion of the heat shield 40 is preferably provided with a reflective coating which reflects a substantial portion of the electromagnetic energy generated by the plasma jet in operation.

The proximate portion of the plasma heat shield 40 is provided with a tapered portion 56 having an internal diameter substantially equal to the external diameter of the sample introduction tube. The proximate portion 56 is also provided with a notched section 58 which provides the function of venting the space between the interior surface of the plasma heat shield 40 and the sample introduction tube 30.

The heat sink 40 may be made out of polished heat resistant metal such as brass. Alternately any heat resistant material may be used with or without a reflective coating. The heat sink 40 insulates the sample introduction tube by (1) reflecting a portion of the energy, (2) dissipating some of the energy by way of the fins, (3) providing an air volume between the surface of the heat sink 40 and the surface of the sample introduction tube 30, and (4) by venting the air volume.

As will be understood by those skilled in the art, the apparatus and method described represent only one operable embodiment of the present invention, and it is intended that the invention be limited only in a manner consistent with and commensurate with the scope of the claims below.

What is claimed is:

1. In a plasma jet device adapted for use in a spectrometer system and having an excitation zone formed by ionized gas, and a sample introduction tube disposed adjacent to the lower region of the excitation zone, the improvement comprising:

means disposed about said sample introduction tube, for insulating the sample introduction tube from heat transfer from the excitation zone, said means comprising a reflective member disposed around said sample introduction tube.

2. The improvement of claim 1 wherein said reflective member comprises:

a hollow cylindrical member having a tapered distal end;

a plurality of radial openings disposed along the longitude of the hollow cylindrical member; and a plurality of fins disposed longitudinally on the hollow cylindrical member.

3. The improvement of claim 2 wherein said hollow cylindrical member and said plurality of fins are integrally formed of a heat resistant metal.

4. A removable heat shield for a sample introduction tube in a plasma jet device comprising:

an elongated hollow cylindrical member having a tapered distal end and a reflective outer surface, said elongated hollow cylindrical member having an internal diameter greater than the external diameter of the sample introduction tube.

5. The heat shield of claim 4 further comprising:
a plurality of radial openings disposed along the longitude of said elongated hollow cylindrical member.

6. The heat shield of claim 5 further comprising:
a plurality of fins disposed longitudinally along the exterior of the elongated hollow cylindrical member.

7. The heat shield of claim 6 wherein said hollow cylindrical member and said fins are integrally formed of heat resistant material.

8. The heat shield of claim 7 wherein said reflective outer surface is polished metal.

9. The heat shield of claim 4 wherein said elongated hollow cylindrical member is provided with a tapered proximate end having an internal diameter substantially equal to the external diameter of the sample introduction tube.

* * * * *